United States Patent [19]

Ebner et al.

[11] 4,263,143

[45] Apr. 21, 1981

[54] PROCESS AND APPARATUS FOR DISPERSING GAS IN A LIQUID

[75] Inventors: Heinrich Ebner, Bonn; Uwe Faust, Fischbach; Wolfgang Sittig, Hofheim, all of Fed. Rep. of Germany

[73] Assignee: Uhde GmbH, Dortmund, Fed. Rep. of Germany

[21] Appl. No.: 81,066

[22] Filed: Oct. 2, 1979

[30] Foreign Application Priority Data

Oct. 12, 1978 [DE]  Fed. Rep. of Germany ....... 2844398

[51] Int. Cl.³ .............................................. C12M 1/08
[52] U.S. Cl. .................................... 210/629; 210/218; 210/219; 261/87; 435/314; 435/315
[58] Field of Search ............................ 210/219–221 R, 210/14, 15, 218, 205–208; 261/36 R, 93, DIG. 75, 87; 435/313–315

[56] References Cited

U.S. PATENT DOCUMENTS 3,954,565  5/1976  Boiko et al. ........................... 435/315
4,029,724  6/1977  Muller et al. ........................... 261/93

FOREIGN PATENT DOCUMENTS 2514196  10/1976  Fed. Rep. of Germany ........... 210/219

*Primary Examiner*—Benoît Castel
*Attorney, Agent, or Firm*—Wilson, Fraser, Barker & Clemens

[57]    ABSTRACT

The present invention relates to a process and an apparatus for dispersing a gas in a liquid flowing within a vertical cycle through two reaction zones arranged in parallel within a reactor, the liquid/gas mixture flowing upwards in the first reaction zone due to the air-lift pump effect and being degassified at the transition from the first reaction zone to the second reaction zone and the completely or partly degassified liquid flowing down and the liquid being remixed with gas (preferably air) at the transition from the second to the first reaction zone below the two reaction zones.

4 Claims, 2 Drawing Figures

PROCESS AND APPARATUS FOR DISPERSING GAS IN A LIQUID

BACKGROUND OF THE INVENTION

The process and apparatus are used for aeration in gas/liquid reactions, preferably for aerating aerobic microbiological processes such as fermentation processes, in particular processes for the production of single-cell proteins.

It is known that, in the case of aerobic fermentation, the growth rate of the microorganisms, or rather their productivity, increases in relation to the degree of aeration. Processes and apparatus for commercial-scale fermentation are known from OS No. 24 36 793 and OS No. 25 54 440. In such processes, a culture solution is recycled in a system which consists of a vertical, partly parallel cycle with two reaction zones, namely rising zone and descending zone. In the rising zone the liquid flows upwards and is mixed with air bubbles. When all or part of the air bubbles on the surface of the liquid have disappeared, the remaining quantity of liquid flows down to the bottom of the descending zone, where it is mixed with air and flows up the rising zone. The air-lift pump action comes into effect.

The air can be admixed to the culture solution either by means of ejectors or by means of rotating aeration pumps as taught in OS No. 23 59 830. When these pumps are used, the culture solution is greatly accelerated, air is drawn in from the atmosphere due to the vacuum thus produced and mixed with the liquid. By appropriately controlling the liquid/gas mixture in the fermentation reactor, a cycle is maintained in which the mixture reaches the surface regularly, where the air on the surface of the liquid is more or less deaerated. Some of the known processes and apparatus also make use of the air-lift pump principle.

The circulation of liquid by means of a pump which handles the entire liquid quantity and which draws in air through holes in the pump wall, produces a high circulation velocity. Reducing the speed of the pump rotor will reduce both the circulation rate of the liquid and the intake of air through the holes in the pump. Thus, control is only possible within a narrow range.

The processes and apparatus which are known at present show characteristics which involve disadvantages for a number of reactions. Thus, a high liquid velocity in the ejector or in the rotary aeration pump is required to produce a vacuum which is sufficient to draw in atmospheric air. Consequently, a very high amount of liquid is circulated per unit of time, thus shortening the remaining reaction period in the rising zone of the fermentation vessel. Moreover, the high outlet velocity causes a heavy physical strain on the microorganisms and damages or destroys some of them. This results in a low conversion rate and possibly even in the undesired production of impurities. In addition, the high outlet velocity from conventional equipment produces a large number of small air bubbles which, although they provide a large material transfer area, have an insufficient rising velocity and thus an excessive residence period in the reaction liquid. In addition, the air-lift pump effect is limited and the separation of the tiny air bubbles on the surface of the liquid is inadequate. The descending liquid stream in the fermenter still contains too much gas per unit of volume. The circulation of gas-laden liquid by means of pumps requires more or bigger equipment.

Another apparatus is described in DE PS No. 1 667 042 which permits a narrow, easily adjustable bubble spectrum to be obtained. This device enables a uniform supply of air to be distributed across the bottom of the reactor with a relatively low, directly pumped quantity of liquid. This produces a uniform rise of bubbles across the reactor. However, at a high gassification rate and with liquids or reaction mixtures that have a tendency to foam, a closed foam layer is formed. Flotation of immiscible particles also occurs. A defined mixing current, i.e., a desired mixing quality cannot be achieved, particularly in the case of large fermenters.

The problem therefore emerged of eliminating the shortcomings of the processes and apparatus which are known at present.

SUMMARY OF THE INVENTION

According to the invention, this problem is solved in that a dispersing device located at the bottom of the reactor mixes a part-stream of the descending liquid from the lower part of the second reaction zone with gas drawn in by this dispersing device and the mixture is centrifuged into the lower part of the first reaction zone with the aid of a diffuser surrounding the rotor of the dispersing device and that this centrifuged mixture flowing upwards is brought together with the main stream of the liquid descending in the second reaction zone and passing from the lower part of the second reaction zone into the first.

DESCRIPTION OF THE PREFERRED EMBODIMENT

According to a further embodiment of the process, the part-stream of the descending liquid which is conveyed by the dispersing device amounts to 5–25% by volume of the entire quantity of liquid descending in the second reaction zone and gas/liquid mixture is centrifuged from the diffuser at a velocity of 3 to 10 m/s. It is a particular advantage if the gas/liquid mixture leaves the diffuser in 8 to 24 part-streams.

The apparatus for performing the process consists of a reactor vessel with the reaction zone for the rising liquid/gas mixture, the reaction zone for the descending liquid and a dispersing device arranged at the bottom of the reactor with driving motor, rotor, diffuser and gas suction line, the two reaction zones being separated by a cylindrical partition, a liquid intake pipe pointing upwards being mounted on the diffuser and protruding into the second reaction zone from below and having a cross-sectional area which is 5–25% of that of the cylindrical partition, and furthermore the upper cover plate of the diffuser being extended by means of a disk to an outside diameter which corresponds to 100–150% of the diameter of the cylindrical partition and the cylindrical partition ending above the disk at such a distance that the remaining transition area for the main stream of the liquid is 30–150% of the disk area between the cylindrical partition and the liquid intake pipe.

According to an embodiment of the invention, the cross-sectional area of the cylindrical partition is 15–50% of the reactor cross-sectional area.

In order to achieve good degassing at the surface of the reaction liquid, the cylindrical partition is equipped with a degassing cone which has a slope of 15°–35° and the upper outer diameter of which is 140–200% of the diameter of the cylindrical partition.

According to a further embodiment of the invention, if the process is to be performed in a reaction vessel with a diameter of more than 6 m, any number of dispersing devices are arranged at the bottom of the reactor, and these are each equipped with a driving motor, a rotor, a diffuser and a gas suction line; a cylindrical partition is arranged above each dispersing device, thus forming a number of second reaction zones which are located in a large first reaction zone, the cross-sectional area of the cylindrical partition corresponding to 15–50% of the proportionate reactor cross-sectional area allotted to each dispersing device, a liquid intake pipe which faces upwards being mounted on each diffuser and projecting from below into the second reaction zone and having a cross sectional area 5–25% of the cross-sectional area of the cylindrical partition, the upper cover plate of each diffuser being extended on the outside by a disk to a diameter corresponding to 100–150% of the diameter of the cylindrical partition and each cylindrical partition ending above the pertaining disk at such a distance that the remaining transition area for the main stream of the liquid is 30–150% of the disk area between the cylindrical partition and the liquid intake pipe.

Alternatively, the partition can be polygonal instead of cylindrical.

The process and apparatus according to the invention overcome the disadvantages of present technology. Optimum circulation of the entire quantity of liquid is achieved by branching off a part-stream of the descending liquid. In this way, parameters such as gas feed rate, reaction time of the gas bubbles, diameter/height ratio of the vessel, discharge rate of the liquid from the circulating apparatus, and thus the production rate, can be adapted to each other without any difficulties. Gentle treatment of the reaction liquid is only achieved by branching off a part-stream, the gentle acceleration of this by the dispersing device and the intake and circulation of the main stream by the air-lift pump effect of the rising aerated part-stream.

An example of the invention is shown in the drawings and is described in detail below.

Figure 1:
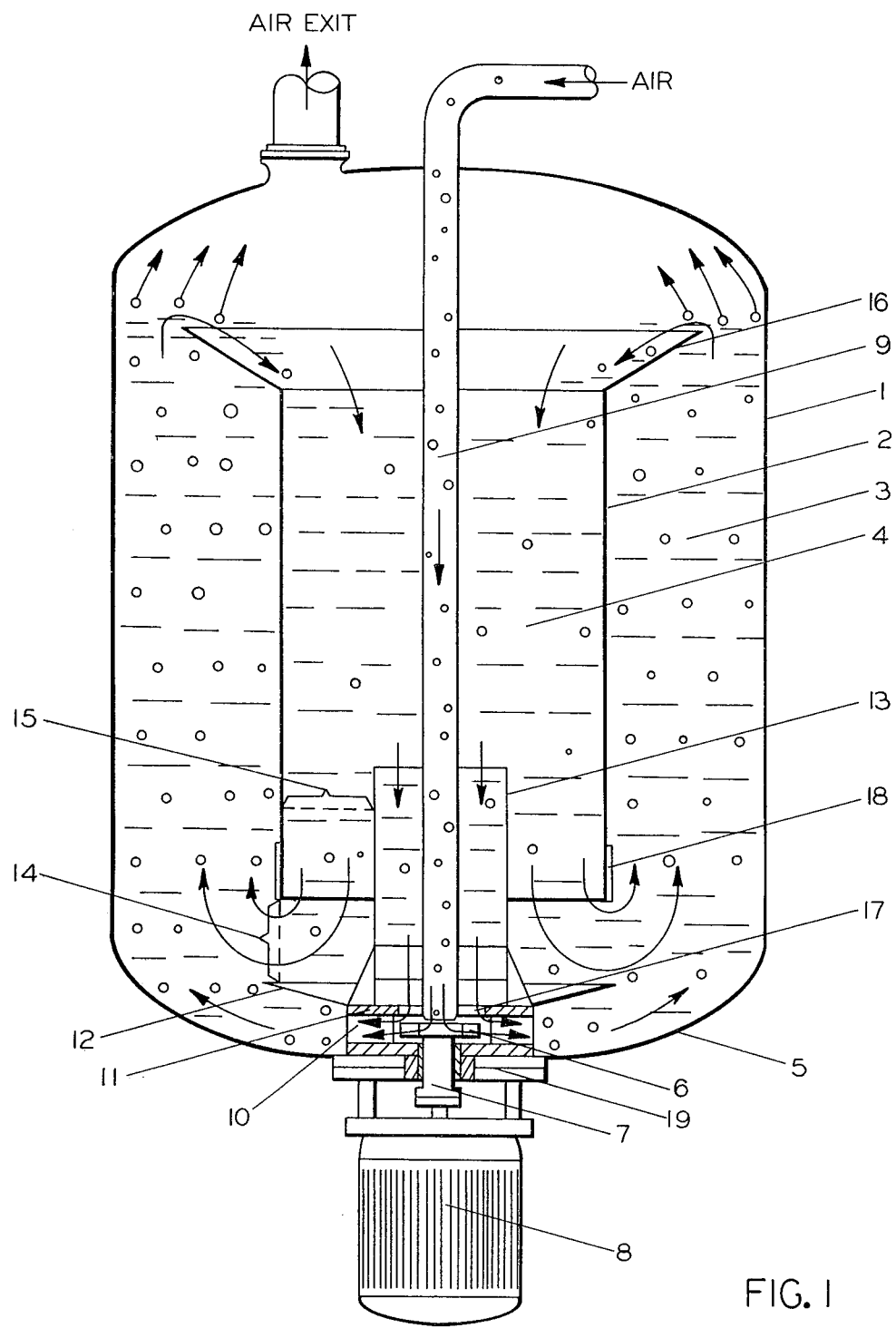
FIG. 1 illustrates the reaction vessel with the aeration device.

The reaction vessel (1) accommodates the cylindrical partition (2), which is freely suspended and arranged centrally. The cylindrical partition divides the vessel interior into the first reaction zone (3) and the second reaction zone (4), the cross-sectional area of the second reaction zone (4) being, for example, 25% of that of the reactor.

The dispersing device basically consists of a rotor (6) located near the reactor bottom (5) and which is surrounded by a diffuser (10). The rotor (6) is mounted on the shaft (7) of the driving motor (8). The shaft (7) is sealed against the reactor by means of a mechanical seal. Air is supplied through the gas suction line (9) which enters the reactor at the top and extends almost to the intake opening of the rotor. The diffuser has a plurality of channels, the cross-section of which depends on the centrifuging rate of the gas/liquid mixture.

The reaction vessel is filled to approximately ¾ of its height with reaction liquid. The upper cover plate (11) of the diffuser (10) has a central liquid intake opening (17) through which liquid flows to the rotating rotor (6). The latter takes in air via the gas suction line (9) as a result of its liquid transfer and sends the gas/liquid mixture through the channels of the diffuser (10) to the outside. The air-lift pump action of the centrifuged air produces a downward liquid flow in the first reaction zone (3), the force of the flow depending on the aeration rate, the filling level and the cross-section of the first reaction zone. The amount of liquid conveyed by the air-lift pump effect is 4–20 times the amount conveyed by the rotor.

Both amounts of liquid flow together to the inside via the degassing cone (16) arranged at the top of the cylindrical partition (2) and downwards in the second reaction zone (4). From the lower cross-section of the second reaction zone (4), the rotor again draws in the amount of liquid corresponding to its discharge capacity through the liquid intake pipe (13) arranged on the upper cover plate (11) of the diffuser (10) and then discharges it together with air through the diffuser. According to the ratio of this quantity of liquid to that which is conveyed by the air-lift pump effect, the inner cross-sectional area of the liquid intake pipe (13) must be 5–25% of the cross-sectional area of the cylindrical partition (2). The liquid conveyed by the air-lift pump effect flows downwards through the remaining annular cross-section (15) of the cylindrical partition (2) and outwards through the gap (14) between the cylindrical partition (2) and the disk (12) which extends the upper cover plate (11) of the diffuser. In order not to disturb this flow and to prevent air from entering the second reaction zone (4) from below, the diameter of the disk (12) must be at least equivalent to the diameter of the cylindrical partition (2). It is advisable that the disk be designed to promote the diversion of the main stream, for example, by making it in the shape of a cone. The main stream is mixed with the part-stream from the diffuser in the lower part of the first reaction zone (3). After a short start-up period, a strong constant circulation sets in when the dispersing device is switched on. The force of the circulation can be regulated within wide limits by the size of the gap (14). For this purpose either the entire cylindrical partition (2) or only a small telescopic cylinder (18) has to be raised or lowered. The liquid/gas mixture leaves the diffuser (10) at a velocity of 3–10 m/s depending on the diameter of the reactor to be aerated. This flow rate is low enough to safely prevent damage to or even destruction of the microorganisms. The upper edge of the cylindrical partition (2) is extended conically to the outside with a slope of 15°–35° up to a diameter of, for example, 160% of the diameter of the cylindrical partition. When passing over this degassing cone (16) the almost horizontally flowing reaction liquid is largely degassed before flowing downwards. The combination of the air-lift pump effect with the liquid transfer of the dispersing device permits the use of naturally-aspirated aerators, for example, according to DE PS No. 1 667 042, for the aeration of very large fermenters without separation occurring, without closed foam layers being formed and without damage to the microorganisms. The following examples show the improvement of the mixing effect by the process and apparatus according to the invention as well as a practical fermentation result compared with a conventional agitated vessel.

EXAMPLE 1

A fermenter of 3 m³ volume equipped with a dispersing device basically according to DE PS No. 1 667 042 was tested to determine the time required for mixing with and without cylindrical partition (2), disk (12) and liquid intake pipe (13). The aeration rate was 0.111 vol./vol. min. in both cases. The effect of the cylindrical partition was only relatively small due to the low aeration rate and the low filling level. The fermenter filled with water contained starch solution as indicator. The approximately 100 ml iodine solution or sodium thiosulphate solution were added alternately into the air intake line and mixed at the bottom with the water by means of the rotor. The time required until the entire contents of the fermenter had changed colour was determined in numerous tests and averaged. The mixing time without the cylindrical partition was 18 seconds and 14 seconds with the circulating device according to the invention. When the aeration rate was increased to 0.5 vol./vol. min., the mixing time decreased to 16 seconds without the cylindrical partition and to 10 seconds with the cylindrical partition. The mixing time was thus reduced to 62.5%. Commercial-scale fermentation processes mainly use larger fermenters with higher aeration rates and greater volumes. There, the mixing time is reduced to about 10% of the time required without the cylindrical partition.

EXAMPLE 2

Fermentation with the bacteria Methylomonas clara and methanol as the only carbon source was performed in a conventional agitated vessel and in the inventive fermenter as shown in FIG. 1 using the inventive process. The composition of the nutrient solution in both cases was: 0.13% by vol. $H_2PO_4$ (85%), 0.07% by vol. trace element solution, 0.11% by wt. $H_2SO_4$, 0.017% by wt. $Na_2SO_4$, 0.018% by wt. $MgSO_4.7H_2O$, 0.01% by wt. $CaCO_3$, 0.007 by wt. $FeSO_4.7H_2O$. The methanol was added with a C limitation controlled automatically via an exhaust air analyzer. The fermentation temperature was 37° C. and the pH value was maintained at 6.7. The filling level was 3.5 m.

| Type of fermenter | Agitated vessel | Fermenter with circulating device |
|---|---|---|
| Filling volume | 20 m³ | 20 m³ |
| Power consumption | 7 kW/m³ | 2.5 kW/m³ |
| Air throughput | 1.2 vol./vol. min. | 1.2 vol./vol. min. |
| Foam elimination | with anti-foam oil | none |
| Maximum productivity | 2 kg/m³/h | 4 kg/m³/h |
| Energy-specific productivity (biomass) | 3.5 kWh/kg | 0.625 kWh/kg |
| Oxygen utilization at maximum productivity | 18% | 35% |
| Reproduction period | 2 h | 2 h |

Example 2 shows the great superiority of the process and apparatus according to the present invention compared with a fermentation process in an agitated vessel with conventional aeration.

The process according to the invention permits the individual parameters for the liquid and the gas to be selected in such a way as to obtain a suitable spectrum of bubble sizes and thus an optimum residence period of the air bubbles in the reaction liquid. Moreover, the air bubbles in the reaction liquid are not as fine as with the spray jet process for example, with the result that degassing of the liquid is easier.

Figure 2:
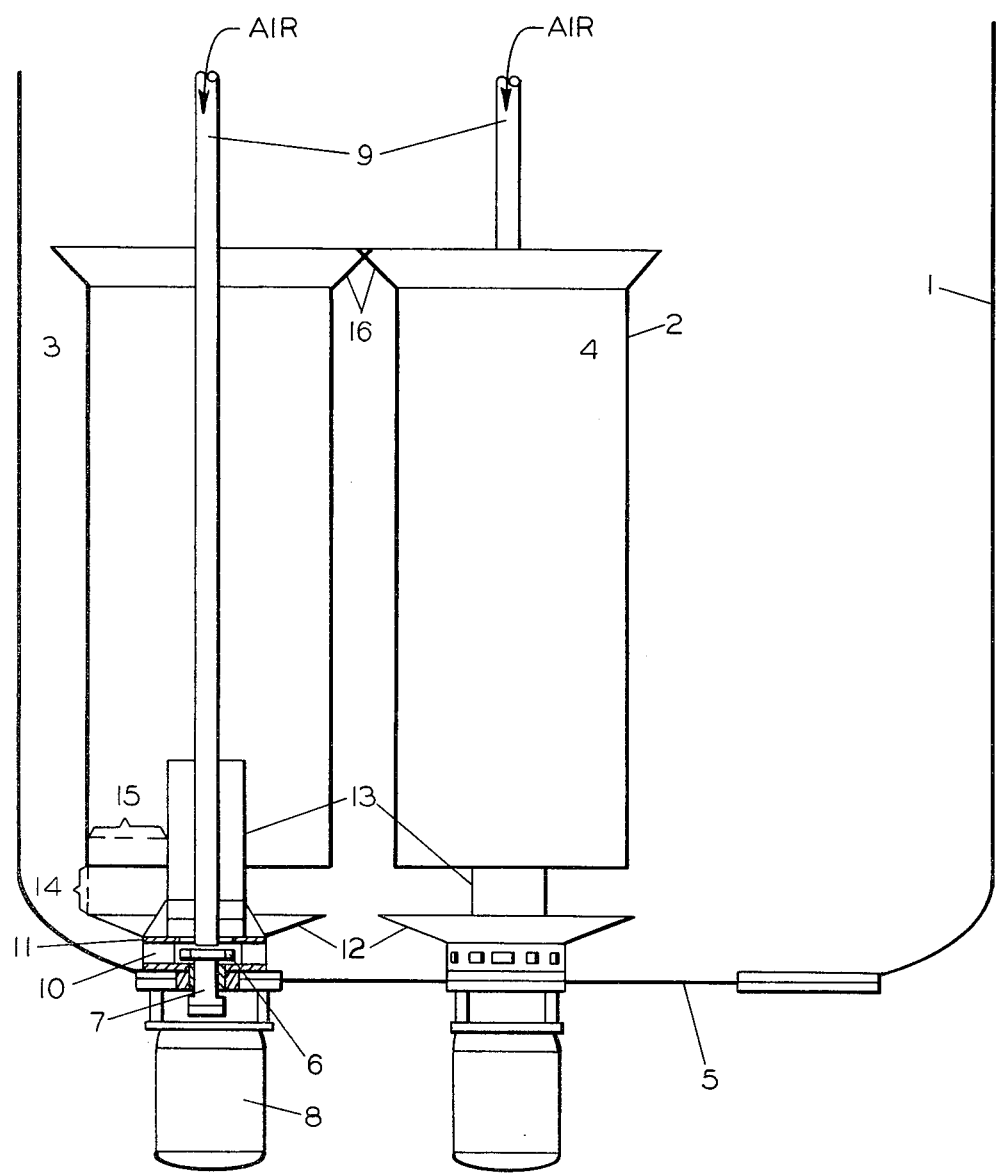
FIG. 2 illustrates a reaction vessel with several aeration devices.

The process according to the invention can also be used as shown by FIG. 2 for vessels with a diameter of more than 6 m. In order to utilize the advantages of the process to the full, several dispersing devices of the same design with driving motor (8), rotor (6), diffuser (10), cover plate (11), liquid intake pipe (13), gas suction line (9), cylindrical partition (2), degassification cone (16) are arranged at the bottom (5) of the vessel (1). A corresponding number of second reaction zones (4) are thus formed and are located in the large first reaction zone (3).

The aeration medium, preferably air, is supplied via in the intake line (9) either from outside or, in the case of a closed cycle or semi-closed cycle, from the free space above the liquid.

The dispersing device can also be designed to draw the air in from the stub end of the shaft. The liquid intake line is then taken to a point outside the vessel wall which is higher than the liquid level in the vessel.

We claim:

1. A process for dispersing gas in a liquid flowing in a vertical cycle through a first reaction zone and a second reaction zone arranged in parallel within a reactor comprising:
   a. filling the reactor with the liquid and flowing a liquid/gas mixture upwards in a first reaction zone due to an air-lift pump effect;
   b. degassifying said liquid/gas mixture at an upper transition zone from said first reaction zone to a second reaction zone;
   c. flowing the completely or partly degassified liquid down through the second reaction zone;
   d. drawing gas into the bottom of said reactor with a dispersing device having a rotor;
   e. mixing 5–25% by volume of the total amount of said descending liquid from the lower part of said second reaction zone with said gas drawn in by said dispersing device;
   f. centrifuging the gas/liquid mixture at 3–10 m/s into the lower part of said first reaction zone with a diffuser surrounding the rotor of said dispersing device, wherein said gas/liquid mixture exiting from said diffuser is 8–24 part-streams;
   g. flowing said centrifuged mixture upwards to contact the main stream of said descending liquid passing from the lower part of said second reaction zone into said first reaction zone.

2. An apparatus for the dispersal of gas in a liquid comprising a reactor vessel, a cylindrical partition in said vessel separating a first reaction zone for rising liquid and a second reaction zone for descending liquid, a dispersing device located at the bottom of said reactor vessel having a driving motor, rotor, diffuser and gas intake line, a liquid intake pipe pointing upwards mounted on said diffuser and protruding into said second reaction zone from below, said intake pipe having a cross-sectional area of 5–25% of said cylindrical partition, wherein the upper portion of the cylindrical partition is equipped with a degassing cone having a slope of 15°–35° and an upper diameter 140–200% of the diameter of said cylindrical partition, an upper cover plate on said diffuser, said plate extended by means of a disk to an outside diameter which corresponds to 100–150% of the diameter of said cylindrical partition, said cylindrical partition ending above said disk at a distance such that the remaining stream of liquid is 30–150% of said disk area between said cylindrical partition and said liquid intake pipe.

3. An apparatus for the dispersal of gas in a liquid as defined in claim 2 wherein the cross-sectional area of the cylindrical partition is 15–50% of the reactor vessel.

4. An apparatus for the dispersal of gas in a liquid as defined in claim 2 or 3 wherein a plurality of said dispersing devices are arranged at the bottom of said reactor, each of said dispersing devices having a driving motor, a rotor, a diffuser and a gas suction line, a plurality of cylindrical partitions arranged above each of said dispersing devices forming a plurality of second reaction zones which are located in a large first reaction zone, the cross-sectional area of said cylindrical partition corresponding to 15–50% of the proportionate cross-sectional area allotted to each of said dispersing devices, a liquid intake pipe facing upwards and mounted on each of said diffusers and projecting from below into said second reaction zone and having a cross-sectional area 5–25% of the cross sectional area of said cylindrical partition, said upper cover plate of each diffuser extended on the outside by a disk to a diameter corresponding to 100–150% of the diameter of said cylindrical partition, each of said cylindrical partitions ending above said disk at such a distance that a remaining transition area for the main stream of liquid is 30–150% of the disk area between said cylindrical partition and said liquid intake pipe.

* * * * *